United States Patent
Cerri et al.

(10) Patent No.: US 6,780,815 B2
(45) Date of Patent: Aug. 24, 2004

(54) PROCESS FOR PREPARING FLUORINATION CATALYST

(75) Inventors: Gustavo Cerri, Parsippany, NJ (US); Yuon Chiu, Denville, NJ (US); Jason T. Stuck, San Jose, CA (US); Hsueh S. Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 109 days.

(21) Appl. No.: 10/186,348

(22) Filed: Jun. 28, 2002

(65) Prior Publication Data

US 2003/0022785 A1 Jan. 30, 2003

Related U.S. Application Data

(60) Provisional application No. 60/301,586, filed on Jun. 28, 2001.

(51) Int. Cl.[7] .......................... B01J 27/06; B01J 27/132; B01J 27/128; B01J 27/125; B01J 20/34
(52) U.S. Cl. ...................... 502/224; 502/228; 502/229; 502/231; 502/34; 502/35; 502/36
(58) Field of Search ................................ 502/224, 228, 502/229, 231, 34–36

(56) References Cited

U.S. PATENT DOCUMENTS

| | | | |
|---|---|---|---|
| 3,717,586 A | 2/1973 | Suggitt et al. .............. 252/439 |
| 3,855,151 A | 12/1974 | Schindel ...................... 252/415 |
| 4,145,311 A * | 3/1979 | von Halasz et al. .......... 502/36 |
| 4,504,599 A | 3/1985 | Sasaki et al. ................ 502/304 |
| 4,578,369 A | 3/1986 | Muller et al. .................. 502/36 |
| 5,036,036 A | 7/1991 | Lerou .......................... 502/317 |
| 5,155,082 A | 10/1992 | Tung et al. .................. 502/228 |
| 5,227,350 A * | 7/1993 | Scott et al. .................... 502/36 |
| 5,334,784 A | 8/1994 | Blake et al. ................. 570/165 |
| 5,668,075 A | 9/1997 | Milam et al. ................ 502/338 |
| 5,739,070 A | 4/1998 | Ebmeyer et al. .............. 502/37 |
| 5,849,658 A | 12/1998 | Shibanuma et al. ........ 502/228 |
| 5,981,813 A * | 11/1999 | Cuzzato et al. ............. 570/166 |
| 6,103,944 A | 8/2000 | Blake et al. ................. 570/165 |
| 6,153,802 A * | 11/2000 | Chiu ........................... 570/123 |
| 6,166,275 A * | 12/2000 | Cerri et al. .................. 570/167 |
| 6,184,172 B1 * | 2/2001 | Bonnet et al. .............. 502/228 |
| 6,337,299 B1 * | 1/2002 | Shibanuma et al. ........ 502/228 |

FOREIGN PATENT DOCUMENTS

| EP | 0 475 693 | * 3/1992 | ............ B01J/38/44 |
|---|---|---|---|
| WO | WO 98/06685 | 2/1998 | |

* cited by examiner

Primary Examiner—Mark L. Bell
Assistant Examiner—Patricia L. Hailey
(74) Attorney, Agent, or Firm—Colleen D. Szuch

(57) ABSTRACT

A process for preparing a fluorination catalyst using a low pressure activating step followed by a high pressure activating step.

6 Claims, No Drawings

PROCESS FOR PREPARING FLUORINATION CATALYST

CROSS-REFERENCE TO RELATED APPLICATION

This application claims priority to U.S. Provisional Application Serial No. 60/301,586 which was filed with the United States Patent and Trademark Office on Jun. 28, 2001 and which is incorporated herein by reference.

FIELD OF THE INVENTION

The present invention relates generally to fluorination catalysts. More particularly, the present invention provides methods and systems for preparing catalysts for use in the fluorination of organic compounds and processes of fluorinating organic compounds.

BACKGROUND OF THE INVENTION

There are numerous processes directed to the manufacture of fluorinated organic compounds. Many of these processes involve the reaction of an organic starting material compound, such an alkane and/or an alkene, with hydrogen fluoride ("HF") in the presence of a fluorination catalyst to produce a desired fluorinated compound or compounds. The product stream from this type of reaction typically includes, in addition to the desired fluorinated organic compound or compounds, unreacted alkane and/or alkene starting materials and unreacted HF. It is common in such processes to separate the unreacted starting materials from the product stream and to recycle those components to the reaction step.

In many prior art processes, the reaction product also includes water. Although water is typically present in relatively minor amounts, its presence in the reaction product stream has been recognized to be undesirable. For example, U.S. Pat. No. 5,334,784—Blake, et al. discloses reacting trichloroethylene and/or 1,1,1-trifluoro-2-chloroethane with HF to produce 1,1,1,2-tetrafluoroethane, using a stoichiometric excess of HF and an increased inventory of catalyst to enhance the conversion efficiency of the process. Blake et al, however, also recognizes that water generated in the reaction or otherwise present in the reactants tends to combine with HF (because of the affinity of HF for water) and, when HF recycle is used, the water content in the product stream tends to build up. Blake et al note that the presence of significant amounts of water in the product stream gives rise to serious obstacles to further treatment of the reaction stream because of the highly corrosive nature of condensate containing HF and water.

Blake et al., and others in the field, have attempted to solve the problem of water in the reaction product by proposing the use of equipment and steps downstream of the fluorination reactor to remove water from the reaction product stream and thereby minimize the amount of water recycled with the unreacted HF.

While approaches of the type suggested by Blake et al. may have some degree of success, they are inherently ineffective in at least one important respect. More particularly, Beck et al. does not acknowledge or recognize that the presence of water generated in or otherwise present during the fluorination reaction may have a deleterious effect on the reaction itself, and the downstream removal solutions are inherently unable to address any such problems.

The present inventors have come to appreciate a need in the art for an improved process for the preparation of fluorination catalyst and a fluorination process, each of which result in improved efficiency, selectivity and/or yield of fluorinated organic compounds (hereinafter sometimes referred to as "fluorocarbons").

SUMMARY

The present inventors have recognized that water generated during the fluorination of organic compounds has a deleterious effect not only on the downstream processing of the reaction product but also on the fluorination reaction itself. Applicants have also come to appreciate that, for at least certain embodiments of the present invention, the extent to which water is generated during the reaction of organic compounds with HF is impacted by the process that is used to prepare the catalyst, and that certain catalyst preparation methods have an unexpected and surprising ability to produce fluorination catalysts which minimize the generation of water during the fluorination of organic compounds.

Applicants have thus discovered a process for preparing fluorination catalyst which comprises exposing a catalytically active compound to an activating agent under conditions effective to achieve substantial thermal and/or water generation stability at a temperature that is at least about 80 relative percent of the operating temperature of the catalyst and a pressure that is at least about 80 relative percent of the operating pressure of the catalyst. In other words, applicants have found that it is preferred to condition the catalyst with an activating agent at or near its operating conditions, and more particularly to bring the catalyst to or near its operating temperature and pressure while removing a substantial amount, and preferably substantially all of, the water and preferably also the heat generated during the activation step.

Applicants have found that in many embodiments it is important to ensure that the catalyst is brought to a state in which it is at a substantially constant temperature under adiabatic conditions, and without exposure to temperature excursions that would be harmful to the effectiveness and/or activity of the catalyst. It is contemplated that many different combinations of steps may be used in view of the present disclosure to bring the catalyst to this desired condition in which it is ready to be used in the fluorination of organic compounds. It is highly preferred, however, that the step of exposing the catalyst to activating agent is performed without allowing the catalyst temperature to exceed about 125 relative percent of the operating temperature of the catalyst. By conditioning catalytically active compounds in accordance with the present invention, the resulting catalyst has a substantially reduced tendency to produce water when used during the fluorination of organic compounds.

As used herein, the term "catalytically active compound" is intended to refer to compounds that tend to catalyze fluorination of organic compounds and to compounds that can be converted, by the present process or others, to such compounds. It is to be understood that this term encompasses not only fresh, unused catalytically active compounds but also compounds that have been previously used as a fluorination catalyst and subsequently regenerated and/or reactivated by the present process or some other process.

As used herein, the term "substantial thermal stability" is intended to refer to conditions in which the rate of change of temperature has slowed to a substantial extent, and preferably is substantially constant for a measurable period of time, under adiabatic conditions. In other words, a catalyst has reached "substanial thermal stability" when the rate of heat generation during the conditioning step is substantially reduced, and preferably is substantially zero. As explained in more detail hereinafter, the preferred exposing step(s) of the present invention result in an exothermic reaction involving the catalyst, and "substantial thermal stability" is achieved when such exotherms are substantially dissipated. Also, substantial thermal stability as used herein produces and is coincident with a gradual reduction, preferably to a substantially constant, relatively low level, of water generated by the conditioning process or step.

As used herein, the term "operating pressure" refers to the pressure or range of pressures at which the catalyst prepared by the present methods is intended to be used, and/or is used, to fluorinate the target organic compound(s). Likewise, the term "operating temperature" refers to the temperature or range of temperatures at which the catalyst prepared by the present methods is intended to be used, and/or is used, to fluorinate the target organic compound(s).

According to one preferred embodiment, the exposing step comprises exposing the catalytically active compound to an activating agent that comprises an activating compound and an inert carrier wherein the concentration of the activating compound in the activating agent increases during at least a portion of the exposing step. According to other preferred embodiments, the temperature of the activating agent and/or the catalyst is increased at least during a portion of the exposing step. In yet other embodiments, the pressure on the catalyst is increased at least during a portion of the exposing step. In highly preferred embodiments, the exposing step comprises increasing each of the concentration, the temperature and the pressure at least during one or more portions of the exposing step.

For example, the exposing step in certain preferred embodiments comprises first exposing the catalytically active compound to an activating agent at a pressure substantially below the operating pressure of the catalyst and then subsequently exposing the catalytically active compound to an activating agent under a second pressure substantially greater than the first pressure. Applicants have found that activating the catalyst using such a stepped pressure technique is highly effective in producing a catalyst that tends to generate a lower concentration of water during the fluorination of the organic compound and hence less water in the reaction product stream.

In general, the exposing step(s) of the present invention tend to fluorinate the catalytically active compound and thereby generate both heat and water. According to preferred embodiments, at least a portion of, and preferably substantially all of, both the heat and water generated from the first, relatively low pressure exposing step are removed from the catalyst, and recycle of the water to the low pressure exposing step is substantially avoided. Although applicants do not wish to be bound by or to any particular theory of operation, the relatively low pressure used in the first exposing step tends to enhance removal from the catalyst of a large proportion of the water that would otherwise be produced during the fluorination of the organic compound (s). Furthermore, the subsequent, higher pressure exposure step conditions the catalyst for the higher operating pressure of the organic fluorination reaction and to further remove water that would otherwise be generated during the organic fluorination reaction. In this way, the amount of water produced by the organic fluorination reaction when the catalyst is brought on-line is substantially lower than when prior art catalysts are used. This in turn results in improved catalyst performance (e.g., selectivity and activity) and permits savings with respect to the type and amount of water removal operations that would otherwise be required as part of the downstream processing required for the target fluorinating reaction.

DETAILED DESCRIPTION OF THE INVENTION

The present invention relates to the preparation of a fluorination catalyst by exposing untreated catalyst to activating agent. The term "untreated catalyst" is used herein in its broad sense to designate a catalytically active compound, or a precursor of a catalytically active compound, which will be subjected to the process steps of the present invention. Thus, the term "untreated catalyst" is intended to include within its meaning not only fresh, untreated catalytic or potentially catalytic compounds, but also to such compounds which have previously been treated by the present invention and/or by other treatment operations. The term is also intended to include catalyst that has previously been used to fluorinate organic compounds and is in need of regeneration or reactivation.

The Catalytically Active Compounds

A large number of catalytically active compounds are known, and it is contemplated that all such compounds can be treated in accordance with the processes of the present invention to produce fluorination catalysts. According to preferred embodiments, fluorination catalysts that may be prepared in accordance with the present invention are those compounds that are catalytically active in the reaction of hydrogen fluoride ("HF") with hydrocarbons, more preferably halogenated hydrocarbons, and even more preferably chlorinated hydrocarbons ("CHCs"). The present methods find particularly advantageous utility in the preparation of catalysts for the fluorination of chlorinated olefins, and particularly perchlorinated olefin, such as perchloroethylene ("PCE") or trichloroethylene ("TCE") to the hydrofluorocarbons ("HFCs") pentafluoroethane (HFC-125) or tetrafluoroethane ("HFC-134a").

Suitable catalytically active compounds are well known in the art, and include various inorganic compounds, for example oxides and halides of metals such as aluminum, cobalt, manganese, iron and chromium. The present invention is particularly well suited for the preparation of chromium based catalysts.

Chromium based fluorination catalysts are typically and preferably based more specifically upon chromia. The chromia may be, for example, fluorinated so that the fluorination catalyst is preferably a chromium oxyfluoride species. Furthermore the chromia may comprise activity promoting amounts of other metals, for example zinc, nickel or cobalt. The chromia based catalyst may be supported on a support system. The support system may be, for example a metal oxide, for example alumina ($Al_2O_3$), magnesia (MgO), a metal fluoride, for example aluminium fluoride and magnesium fluoride or the support system may be an activated carbon.

Chromium based catalytically active compounds particularly useful in accordance with the present invention are disclosed in U.S. Pat. No. 5,155,082, which is incorporated herein by reference.

The Preparation of Fluorination Catalyst

The present methods can be carried out in a wide variety of environments and in batch, continuous, and/or semi-continuous operations. It is generally preferred, however, that the methods are carried out in continuous or semi-continuos operations. Furthermore, it is generally preferred that the untreated catalyst of the present invention is provided in the same reaction vessel that will be used for fluorination of the organic compound. In this way, the catalyst will be in place and ready for use in fluorination process of the present or other methods upon completion of the preparation aspects of the present invention. The appropriate piping, valving and the like need for such an arrangement are well know in the art and need not be described in detail herein.

The Drying Step

The catalytically active compound to be processed in accordance with the present invention can be provided substantially free of water or it can be subjected to a drying step, which preferably produces a compound substantially free of unbound water. When used, the drying step preferably comprises passing a drying gas, preferably nitrogen, over and in intimate contact with the untreated catalyst so as to carry away a substantial portion of any unbound water present in, on or otherwise associated with the untreated catalyst. It is preferred that the drying step be carried out at about atmospheric pressure with the catalyst at a temperature substantially above room temperature, even more preferably at a temperature of from about 65° C. to about 350° C. Preferably, the drying step comprises a stepped temperature process including raising the temperature of the catalyst from about room temperature to about 80° C. to about 100° C. for a period of time of from about 2 hours to about 36 hours, followed by rasing the temperature of the catalyst to about the operating temperature of the catalyst, preferably about 300° C.–375° C., for a period of about 8 hours. An in-line moisture analyzer is preferably installed to monitor the water content of the effluent stream. The preferred temperature increasing steps are preferably initiated in response to a relatively diminished water content in the effluent stream, as indicated by the monitoring step.

Any heating means known in the art may be used to heat the catalyst to the indicated ranges. For example, the catalyst may be heated directly by heating the drying gas or indirectly by heating the vessel containing the catalyst.

The Low Pressure Exposing Step

The preferred embodiments of the present methods importantly include exposing the catalytically active compound to an activating agent at a first pressure substantially below the operating pressure of the catalyst. As used herein, the term "activating agent" refers to any compound or combination of compounds which improve the activity of the catalytically active compound to the desired target compound. Although many such agents are available and useful in accordance with the broad aspects of the present invention, the activating agent preferably comprises a compound which tends to fluorinate the untreated catalyst, hereinafter sometimes referred to as a fluorinating agent. According to preferred embodiments, the activating agent comprises an activating gas that comprises a fluorinating agent such as HF, and even more preferably a combination of a fluorinating agent and an inert carrier gas such as nitrogen.

When the preferred combination of fluorinating agent and inert carrier is used, it is preferred that the activating gas comprise from about 0.5 wt % to about 99 wt % of fluorinating agent, with the balance being inert carrier gas.

The preferred low pressure exposure step of the present invention results in fluorination of the untreated catalyst, which in turn results in the generation of water and of heat. Important embodiments of the present invention involve the step of removing from the catalyst both the heat and the water, and preferably substantially all of water and a substantial portion of the heat, generated during the low pressure exposure step. It will be apparent to those skilled in the art in view of the present disclosure that it is acceptable, and in some cases may even be desirable, to allow some portion of the exotherimic reaction heat to be absorbed by the catalyst and contribute to raising of the temperature of the catalyst in accordance with other aspects of the present invention described in more detail hereinafter.

Numerous heat and water removal techniques can be used in accordance with the present invention, and all such steps are encompassed within the scope hereof. With respect to the water removal step, it is preferred that the water is removed as a feature of the exposure step. For example, it is preferred that the activating gas is maintained in intimate contact with the catalyst for a time sufficient to not only activate the catalyst but also to allow a substantial portion of the generated water to be absorbed by, entrained in, otherwise carried by the activating gas. Removal of the activating gas from catalyst also then results in removal of water from the catalyst. Similarly, the heat can be removed from the catalyst by allowing the activating gas to absorb at least a portion of the heat of reaction and to then carry the heat away from the catalyst as the gas leaves the conditioning system. In addition, other techniques can be use to remove the heat of the exothermic reaction from the catalyst, such as external cooling of the vessel containing the catalyst.

It is generally preferred that the low pressure exposure step is conducted as a continuous process in which the activating gas is passed over, and preferably in intimate contact with, the catalyst and then removed from the catalyst through an outlet nozzle or port in the vessel containing the catalyst. In such embodiments, the residence time of the activating gas in contact with the catalyst can vary widely depending on numerous factors associated each individual application, such as the type and amount of the catalyst, the type and amount of activating gas, and like factors. In general, the residence time of the activating gas in the low pressure exposing step is preferably from about 0.01 hour to about 10 hours, and even more preferably from about 0.5 hours to about 5 hours.

In highly preferred embodiments, the step of exposing the catalyst to activating gas at low pressure comprises increasing the percentage of fluorinating agent in the activating gas during the course of the low pressure exposing step from an initial, relatively low concentration to a final, relatively high concentration. It is contemplated that the starting concentration and ending concentration of fluorinating agent, and the rate of increase of fluorinating agent concentration may vary widely depending on the particulars of each application, and all such variations are within the broad scope hereof. However, for embodiments in which the fluorinating agent is HF and the inert carrier gas is nitrogen, it is preferred that the concentration of HF in the activating gas in this low pressure exposing step is initially about 0.5 wt. %–5 wt. % and finally about 15 wt. %–100 wt. %.

According to highly preferred embodiments, the low pressure exposing step comprises initially exposing the catalyst to an activating gas comprising about 1 wt. % HF and 99 wt. % nitrogen. This exposure sub-step preferably is conducted under conditions effective to maintain the temperature of the catalyst below about 215° C. and for a time sufficient to achieve a substantially constant catalyst temperature under adiabatic conditions. In other words, the introduction of activating agent to the untreated catalyst will generally result in the generation of heat in the catalyst bed as a result of exothermic reaction, and the exposure step preferably includes the step of removing heat from the catalyst at a rate sufficient to prevent the catalyst temperature from exceeding about 215° C. (420° F.) until the reaction exotherms substantially cease.

Once the catalyst is exposed to an activating gas having a first, relatively low HF concentration, the percentage of HF in the activating gas is increased one or more times. Since each increase in the concentration of fluorinating compound will produce additional exothermic reactions, which generally involve the generation of water, and each increase in concentration is preferably associated with a water removing step and a heat removing step to keep the catalyst temperature below a predetermined target for that concentration range. In preferred embodiments in which the initial fluorinating agent is present in an amount of from about 1 wt. % to about 3 wt % of the activating gas, the concentration increasing step comprises increasing the concentration of the fluorinating agent, preferably gradually, to about 20–100 wt %, most preferably about 35 wt %. Preferably, each concentration increasing step is accompanied by a heat and a water removing step as described above.

After the concentration is increased to its maximum and the exothermic heat of reaction is substantially removed, optionally but preferably, the catalyst temperature is increased to within a range of from about 300° C. to about 375° C., with a temperature in a range of from about 320° C. to about 360° C. being more preferred, and a temperature of about 350° C. being most preferred. The temperature increasing step can utilize any well known technique for raising catalyst temperature, including by heating the inlet temperature of the activating gas and/or heating the vessel in which the catalyst is contained. The step of increasing temperature may also cause reaction exotherms, and it is preferred that once the maximum temperature is reached and these exotherms substantially cease, then the catalyst temperature is reduced by cooling to about 200° C. to about 300° C., more preferably to about 220° C. to about 275° C., and even more preferably to about 250° C.

As mentioned above, it is preferred that the low pressure exposing step is a continuous process comprising continuously introducing one or more activating gas input streams to a reaction vessel containing the untreated catalyst and continuously removing, preferably on a equal mass basis relative to the gas inlet stream, one or more gas output streams that have contacted and been exposed to the catalyst. Optionally, but preferably, this activating gas output stream is treated by one or more scrubbing operations to remove water, acid, and/or other unwanted by-products from the stream. Optionally, the scrubbed inert gas can be recycled for use in the activating gas input stream, however this is not preferred because of the tendency of even the scrubbed stream to carry water back to the conditioning operation. Preferably, there is substantially no recycle of any water that may be contained in the output stream, and even more preferably there is no recycle of any water to the conditioning step.

The pressure used in accordance with the first exposing step of the present invention can vary widely depending on numerous factors particular to each particular application, provided the pressure is substantially less than the operating pressure of the organic fluorination reaction in which the catalyst is to be used. In general, the pressure in this initial exposing step is preferably at least about 25 psig less than, and even more preferably at least about 50 psig less than, the pressure in the second exposing step described below. In many preferred embodiments, the pressure of the low pressure exposing step ranges from about atmospheric pressure to about 25 psig, with atmospheric being preferred.

The High Pressure Exposing Step

The present methods also importantly include exposing the catalytically active compound, preferably after the lower pressure exposing step described above, to an activating agent at second pressure substantially above the pressure of the first exposing step. According to preferred embodiments, the second exposing step is carried out at a pressure of from about 15 psig to about 200 psig and more preferably from about 30 psig to 150 psig. In preferred embodiments, the pressure in the second exposing step is a variable pressure starting initially at substantially below the operating pressure of the catalyst but substantially above the pressure in first exposure step, and increasing to about the operating pressure of the catalyst.

It is contemplated that the preferred high pressure exposure step of the present invention results in further fluorination of the catalyst which, as in the low pressure step, results in the generation of water and of heat. Importantly, as with the low pressure step, the high pressure exposure step also preferably includes removing from the catalyst both the heat and the water, and preferably substantially all of the water and a substantial portion of the heat, generated during the high pressure exposure step. Although applicants do not intend to be bound by or to any particular theory of operation, it is believed that the relatively high pressures used in the second exposing step tend to force the activating agent deep into the pores of the catalyst and thereby achieve a more thorough activation of the catalyst.

Numerous heat and water removal techniques can be used in accordance with the present invention, and all such steps are encompassed within the scope hereof. With respect to the water removal step, it is preferred that the water is removed as a feature of the exposure step. For example, it is preferred that the high pressure activating gas is maintained in intimate contact with the catalyst for a time sufficient to not only further activate the catalyst but also to allow a substantial portion of the generated water to be absorbed by, entrained in, or otherwise carried by the activating gas. Removal of the activating gas from catalyst also then results in removal of water from the catalyst. Similarly, the heat can be removed from catalyst by allowing the activating gas to carry the heat away from the catalyst. In addition, other techniques can be use to remove the heat of the exothermic reaction from the catalyst, such as external cooling of the vessel containing the catalyst.

It is also generally preferred that the high pressure exposure step is conducted as a continuous process in which the activating gas is passed over and in intimate contact with the catalyst and then removed from the catalyst by passing the gas through the vessel containing the catalyst. In such embodiments, the residence time of the high pressure activating gas in contact with the catalyst can vary widely depending on numerous factors associated each individual application, such as the type and amount of the catalyst, the type and amount of activating gas, and like factors. In general, the residence time of the activating gas in the high pressure exposing step is preferably from about 0.01 hours to about 15 hours, and even more preferably from about 0.5 hours to about 10 hours.

In preferred embodiments, the catalyst in the second, high pressure exposing step is initially exposed to activating gas at an initial pressure that is at least about 50 psi less than the operating pressure of the catalyst and is maintained at a temperature that is substantially below the operating temperature of the catalyst, and even more preferably at least about 100° C. below the operating temperature of the catalyst. According to preferred embodiments, the initial pressure of the activating gas is from about 20 psig to about 45 psig, and temperature of the catalyst is maintained below about 300° C., and even more preferably below about 250° C., during this initial high pressure exposure. The initial phase of the high pressure exposure step is preferably maintained for a time sufficient to substantially dissipate the exotherm of created by the exposure step. One method for ensuring that the exotherm has been dissipated is to achieve a substantially constant catalyst temperature under adiabatic conditions.

Once thermal stability is achieved at the conclusion of the initial phase of the high pressure exposing step, the temperature of and the pressure on the catalyst is preferably further increased to within at least about 10 relative percent of the operating temperature and pressure of the catalyst, and even more preferable to about the operating temperature and pressure of the catalyst.

According to preferred embodiments, the operating temperature of the catalyst is in a range of from about 200° C. to about 400° C., more preferably from of from about 320° C. to about 375° C., and even more preferably about 350° C. The operating pressure of the catalyst is preferably from about 50 psig to about 200 psig, with about 100 psig being most preferred in certain embodiments. The catalyst is preferably brought to about the operating temperature and pressure of the catalyst in a fashion that results in substantial thermal stability at these conditions. More particularly, it is contemplated that raising the catalyst temperature and pressure will generate exothermic reaction conditions in the catalyst bed, and this heat of reaction is preferably substantially removed from the catalyst until thermal stability at or about the operating temperature and pressure is substantially achieved.

According to ceratin preferred embodiments, the step of raising the catalyst temperature/pressure to the operating temperature/pressure comprises first raising the temperature of the catalyst to the operating temperature while removing any exothermic heat of reaction until thermal stability is substantially achieved. The catalyst is then cooled to below the operating temperature, preferably to a temperature of from about 20° C. to 80° C. below the operating temperature, and when the catalyst is so cooled, the pressure is increased to about the operating pressure of the catalyst. Preferably, any exothermic heat of reaction generated by the pressure increase is removed until thermal stability is once again substantially achieved. Finally the temperature of the catalyst is raised to about the operating temperature, and the catalyst is then ready for use in the fluorination of organic compounds in accordance with the present invention.

The activating agent for use in the high pressure exposing step can be selected in accordance with the same parameters described above, and may be the same or different than the activating agent used in the low pressure exposing step. In general, the preferred embodiments of the invention utilize a high pressure activating agent in the form of an activating gas which comprises a major proportion of fluorinating compound(s), more preferably at least about 80 wt. % of fluorinating compound(s), and even more preferably at least about 95 wt. % of fluorinating compound(s). In highly preferred embodiments, the activating gas in the high pressure exposing step consists essentially of fluorinating compound(s), and even more preferably HF.

As mentioned above, it is preferred that the high pressure exposing step is a continuous process comprising continuously introducing one or more activating gas input streams to a reaction vessel containing the catalyst and continuously removing, preferably on a substantially equal mass basis relative to the gas inlet stream(s), one or more gas output streams that have contacted and been exposed to the catalyst.

Optionally, but preferably, the activating gas output stream from the high pressure exposing operation is dehydrated to produce a water lean stream and water rich stream. According to preferred embodiments, the dehydration step comprises introducing the activating gas output stream into a dehydrating distillation column, and preferably a packed distillation column, having at least one overhead stream that has a relatively low concentration of water relative to the activating gas output stream and at least one bottoms stream that has a high concentration of water relative to the activated gas output stream.

As mentioned above the gas output stream from the high pressure exposing step comprises, in addition to the fluorinating compound, such as HF, a minor amount of water. In certain embodiments, the gas output stream comprises less than about 10 wt % water, and even more preferably less than about 5 wt % water. It is preferred that the water separation step produce a water lean stream or streams that togther comprise at least about 75 wt %, and even more preferably at least about 95 wt %, of the fluorinating agent present in the activating gas output stream and no greater than about 20 wt %, more preferably no more than about 10 wt %, and even more preferably no more than 5 wt % of the water present in the activating gas output stream.

Preferably a substantial portion of the fluorinating compound, and particularly HF, present in the activating gas output stream is recycled to the high pressure exposing step of the present invention. Furthermore, it is preferred that only a minor amount, and preferably less than about 10 wt % of the water in the activating gas output stream is recycled to the high pressure exposing step. One means for achieving this function is to recycle the preferred water lean stream described above to the high pressure exposing step. A substantial portion of the water in output stream is preferably removed by the dehydrating column. The water lean stream from the dehydrating column is preferably substantially anhydrous.

EXAMPLES

A fluorination catalyst is loaded into a reaction vessel intended for use in the fluorination of PCE to HFC-125. The catalyst has an operating pressure of about 100 psig and an operating temperature of about 350° C.

Drying

The catalyst is first dried by continuously introducing into the reaction vessel a drying gas consisting of nitrogen at about atmospheric pressure and withdrawing an equal amount of nitrogen gas. The temperature of the nitrogen drying gas, and hence the catalyst, is maintained for a period of 18 hours at about 100° C. The temperature of the nitrogen drying gas, and hence the catalyst, is then increased to about 350° C. and maintained at about this temperature for about 8 hours.

Initial Activation

The reactor is then cooled to about ambient temperature and the an activating agent consisting of about 99 percent by weight of nitrogen and about 1 percent by weight of HF is introduced into the reactor at a rate of about 10 pounds per hour per 150 pounds of catalyst. The catalyst reacts with the activating agent and a reaction exotherm is initially developed in the reactor catalyst bed, and water is generated as a result of the activation. The heat of reaction is removed at a rate sufficient to maintain the reactor temperature below about 215° C., and the generated water is continuously removed from the catalyst as the activating agent is continuously removed from the reactor.

The concentration of HF in the activating agent is then increased to about 2 percent by weight. Once again, the catalyst reacts with the new activating agent and a reaction exotherm is initially developed in the reactor catalyst bed, and increased water concentration is generated as a result of the activation. The heat of reaction is removed at a rate sufficient to maintain the reactor temperature below about 215° C., and the generated water is continuously removed from the catalyst as the activating agent is continuously removed from the reactor. Sufficient time is permitted to allow the exotherm to be substantially dissipated such that the system is again at substantially steady state conditions and the water content of the effluent is has decreased to a substantially steady state base line value.

The concentration of HF in the activating gas is then gradually increased to about 25% by weight. Once again, the catalyst reacts with the new activating agent as the concentration of HF is increased, and reaction exotherms are developed in the reactor catalyst bed, and increased water concentration is generated as a result of the activation. The heats of reaction are removed at a rate sufficient to maintain the reactor temperature below about 215° C., and the generated water is continuously removed from the catalyst as the activating agent is continuously removed from the reactor. Eventually, the heat of reaction and the generated water in the reactor effluent gradually decrease to approach substantially steady state conditions in which the water content in the effluent is a substantially steady state base line.

The reactor temperature is then increased to about 350° C. by heating the HF and nitrogen gas mixture. The temperature increase in the catalyst causes additional reaction exotherms in the reactor catalyst bed, and water concentration is initially increased. The heats of reaction are removed at a rate sufficient to maintain the reactor temperature of no greater than about 350° C., and the generated water is continuously removed from the reactor. Eventually the heat of reaction and the generated water in the reactor effluent gradually decrease to approach substantially steady state conditions in which the water content in the effluent is a substantially steady state base line.

The reactor is then cooled by cooling the fluorinating gas mixture (HF and nitrogen) to a temperature of about 230° C.

During the above described drying and initial activation steps, no substantial portion of the reactor effluent is recycled to the reactor. The reactor effluent is treated and disposed of as appropriate according to known methods.

Deep Activation

A new activating agent consisting essentially of HF is then introduced to the reactor at a rate of about 10 pounds per hour per 150 pounds of catalyst. The catalyst reacts with the HF and a reaction exotherm is initially developed in the reactor catalyst bed, and water is generated as a result of the activation. The heat of reaction is removed at a rate sufficient to maintain the reactor temperature below about 290° C. while maintaining the pressure in the reactor below about 30 psig. The generated water is continuously removed from the reactor via the reactor effluent.

The effluent from reactor is introduced to a dehydrating column of known design which separates the effluent into a water rich stream, which contains about 95% of the water in the reactor effluent. The water lean stream is continuously recycled to the reactor. The total feed (fresh feed plus recycle) of activating agent, which now consists of HF and water, is maintained at about 10 pounds per hour per 150 pounds of catalyst.

The continued HF feed causes additional reaction exotherms in the reactor catalyst bed, and the heats of reaction are removed at a rate sufficient to maintain the reactor temperature of no greater than about 290° C., and the generated water is continuously removed from the catalyst with the activating agent as the activating agent is continuously removed from the reactor. When the HF rate is at about 10 pounds per hour per 150 pounds of catalyst, the feed to the reactor consists of essentially 99.95 percent by weight of HF and 0.05 percent by weight of water.

The reactor temperature is then slowly increased to about 360° C. by heating the incoming HF stream. The temperature increase in the catalyst causes additional reaction exotherms in the reactor catalyst bed, and water concentration is initially increased. The heats of reaction are removed at a rate sufficient to maintain the reactor temperature of no greater than about 360° C., and the generated water is continuously removed from the catalyst as the activating agent is continuously removed from the reactor. Eventually the heat of reaction and the generated water in the reactor effluent gradually decrease to approach substantially steady state conditions in which the water content in the effluent is a substantially steady state base line.

The reactor is then cooled by reducing the temperature of the HF feed stream and the reactor pressure is slowly increased to about 100 psig. This pressure increase causes additional reaction exotherms in the reactor catalyst bed, and water concentration is initially increased. The heats of reaction are removed at a rate sufficient to maintain the reactor temperature of no greater than about 360° C., and the generated water is continuously removed from the catalyst as the activating agent is continuously removed from the reactor. Eventually the heat of reaction and the generated water in the reactor effluent gradually decrease to approach substantially steady state conditions.

What is claimed is:

1. A process for preparing a catalyst useful in the fluorination of an organic compound comprising: exposing, in a low pressure exposing step, a catalytically active compound to a first activating agent at a first pressure substantially below the operating pressure of the organic fluorination reaction; exposing said catalytically active compound to said first activation agent at about the operating temperature and pressure of the catalyst under conditions effective to achieve substantially steady state conditions at about said operating temperature and pressure; and removing from said catalytically active compound said first activating agent.

2. The process in accordance with claim 1 wherein said process further comprises, subsequent to said low pressure exposing step, exposing said catalytically active compound to a second activating agent, which is the same as or different than the first activating agent, at a second pressure substantially above said first pressure and removing from said catalytically active compound said second activating agent.

3. The process of claim 2 further comprising separating a substantial portion of any water present in the activating agent removed from the catalyst in said high pressure removing step into a water rich product and a water lean product and recycling at least a portion of said water lean product to said high pressure exposing step.

4. A process for preparing a catalyst useful in the fluorination of an organic molecule with hydrogen fluoride comprising:

a. fluorinating a catalytically active compound with a first activating gas at a first pressure substantially below the operating pressure of the organic fluorination reaction to produce a reaction product comprising activating gas and water;

b. substantially avoiding recycling any substantial portion of said water to said fluorination step (a);

c. fluorinating the catalytically active compound with a second activating gas, which is the same as or different than the first activating gas, at a second pressure substantially above said first pressure to produce a reaction product containing activating gas and water; and d. separating a substantial portion of the water present in the reaction product of fluorination step (c) into a water rich product and a water lean product and recycling at least a portion of said water lean product to reaction step (c).

5. A process for activating a chromium oxyfluoride catalyst to produce an activated catalyst useful in the vapor phase fluorination reaction of a halohydrocarbon with hydrogen fluoride comprising:

a. drying the catalyst to obtain a substantially moisture free catalyst;

b. fluorinating the dried catalyst with a first activating gas at a first pressure substantially below the operating pressure of the catalyst to produce a reaction product containing activating gas and water while maintaining the temperature of the catalyst below about 215° C. for a time sufficient to achieve a substantially constant catalyst temperature under adiabatic conditions;

c. substantially avoiding recycling of any reaction product of the fluorination step (b) to said step (b);

d. fluorinating the dried catalyst with a second activating gas, which is the same as or different than the first activating gas, at a second pressure substantially above said first pressure to produce a reaction product containing activating gas and water while maintaining the temperature of the catalyst above about 215° C. and below about 375° C. (about 700° F.) for a time sufficient to achieve a substantially constant catalyst temperature under adiabatic conditions; and e. separating a substantial portion of the water present in the reaction product of fluorination step (d) into a water rich product and a water lean product and recycling at least a portion of said water lean product to reaction step (d).

6. A process for activating a fluorination catalyst to produce an activated catalyst useful in the vapor phase fluorination of a halohydrocarbon with hydrogen fluoride comprising:

a. loading untreated catalyst into a fluorination reaction vessel;

b. drying the catalyst by: (1) passing nitrogen gas over the catalyst at about atmospheric pressure and a temperature of from about 80° C. (about 175° F.) to about 100° C. (about 212° F.) for about 18 to about 36 hours; and then (2) heating said nitrogen gas to a temperature of about 350° C. (about 660° F.) and passing said heated nitrogen gas over said catalyst for about 8 hours;

c. cooling the heated catalyst of step (b) to a temperature of about 175° C. (about 350° F.);

d. passing over the cooled catalyst of step (c) an activating gas at about atmospheric pressure while maintaining the temperature of the catalyst below about 215° C. (about 420° F.) for a time sufficient to achieve a substantially constant catalyst temperature under adiabatic conditions, said first activating gas comprising from about 75 wt. % to about 99 wt. % of nitrogen and from about 1 wt. % to about 25 wt. % of hydrogen fluoride;

e. increasing the temperature of the catalyst produced in step (d) to about 350° C. (about 660° F.) while maintaining said catalyst at about atmospheric pressure and while passing over the catalyst an activating gas comprising about 75 wt. % nitrogen and about 25 wt. % hydrogen fluoride for a time sufficient to achieve a substantially constant catalyst temperature under adiabatic conditions;

f. cooling the catalyst produced in step (e) to a temperature of about 250° C. (about 450° F.); and g. passing over the catalyst a second activating gas consisting essentially of fresh hydrogen fluoride and recycled dehydrated hydrogen fluoride at about a pressure of from about 30 psig to about 100 psig while maintaining the temperature of the catalyst at a temperature which is not substantially greater than the desired fluorination reaction temperature for a time sufficient to achieve a substantially constant catalyst temperature under adiabatic conditions.

* * * * *